United States Patent
Hannemann et al.

(10) Patent No.: US 10,827,285 B2
(45) Date of Patent: Nov. 3, 2020

(54) METHOD FOR OPERATING A HEARING AID AND HEARING AID

(71) Applicant: SIVANTOS PTE. LTD., Singapore (SG)

(72) Inventors: Ronny Hannemann, Buckenhof (DE); Daniel J. Strauss, Saarbruecken (DE); Farah Corona-Strauss, Saarbruecken (DE)

(73) Assignee: Sivantos Pte. Ltd., Singapore (SG)

( * ) Notice: Subject to any disclaimer, the term of this patent is extended or adjusted under 35 U.S.C. 154(b) by 151 days.

(21) Appl. No.: 16/102,983

(22) Filed: Aug. 14, 2018

(65) Prior Publication Data

US 2019/0052977 A1 Feb. 14, 2019

(30) Foreign Application Priority Data

Aug. 14, 2017 (DE) .................. 10 2017 214 163

(51) Int. Cl.
*H04R 25/00* (2006.01)
*H04R 3/00* (2006.01)
(Continued)

(52) U.S. Cl.
CPC ........... *H04R 25/40* (2013.01); *A61B 5/0478* (2013.01); *H04R 3/00* (2013.01); *H04R 25/70* (2013.01);
(Continued)

(58) Field of Classification Search
CPC ...... H04R 25/40; H04R 25/43; H04R 25/505; H04R 25/70; H04R 25/552; H04R 2225/021; H04R 2225/41; H04R 2225/67
(Continued)

(56) References Cited

U.S. PATENT DOCUMENTS 6,330,339 B1 12/2001 Ishige et al.
8,559,645 B2 * 10/2013 Corona-Strauss ..... H04R 25/70
381/312
(Continued)

FOREIGN PATENT DOCUMENTS

EP 2200347 A2 6/2010
EP 2357851 A1 8/2011
(Continued)

OTHER PUBLICATIONS

Sullivan, J. et al.: Neural decoding of attentional selection in multispeaker environments without access to clean sources. In: Journal of Neural Engineering, 14, 2017, S. 1-14.
(Continued)

*Primary Examiner* — Huyen D Le
(74) *Attorney, Agent, or Firm* — Laurence A. Greenberg; Werner H. Stemer; Ralph E. Locher

(57) ABSTRACT

A method operates a hearing aid for a user. A neuronal signal of the user is measured in the method and a listening effort of the user is determined therefrom. Both an intensity of the listening effort and a hearing direction are determined from the neuronal signal. The intensity and the hearing direction form a hearing vector. A mode of operation of the hearing aid is adapted or set depending on the hearing direction, for the purposes of reducing the intensity of the listening effort.

22 Claims, 2 Drawing Sheets

(51) Int. Cl.
*A61B 5/0478* (2006.01)
*H04R 1/10* (2006.01)
*H04R 5/033* (2006.01)

(52) U.S. Cl.
CPC .......... *H04R 1/1008* (2013.01); *H04R 1/1016* (2013.01); *H04R 1/1041* (2013.01); *H04R 5/033* (2013.01); *H04R 25/552* (2013.01); *H04R 2225/021* (2013.01); *H04R 2225/41* (2013.01); *H04R 2225/55* (2013.01)

(58) Field of Classification Search
USPC ........ 381/23.1, 60, 312, 314, 321, 326, 313; 600/25, 559
See application file for complete search history.

(56) References Cited

U.S. PATENT DOCUMENTS

| | | | |
|---|---|---|---|
| 8,971,558 B2* | 3/2015 | Lunner | H04R 25/00 381/312 |
| 2010/0160714 A1 | 6/2010 | Chua et al. | |
| 2011/0150253 A1 | 6/2011 | Corona-Strauss et al. | |
| 2012/0177233 A1 | 7/2012 | Kidmose et al. | |
| 2014/0098981 A1 | 4/2014 | Lunner | |
| 2015/0181355 A1 | 6/2015 | Pedersen | |
| 2016/0119726 A1 | 4/2016 | Pontoppidan et al. | |
| 2016/0320840 A1 | 11/2016 | Hwang et al. | |
| 2019/0052978 A1* | 2/2019 | Hannemann | A61B 5/04888 |
| 2019/0182606 A1* | 6/2019 | Petersen | A61N 1/36036 |

FOREIGN PATENT DOCUMENTS

| | | |
|---|---|---|
| JP | H09182193 A | 7/1997 |
| JP | 2012533248 A | 12/2012 |
| JP | 2014112856 A | 6/2014 |
| JP | 2015056829 A | 3/2015 |
| JP | 2015136100 A | 7/2015 |
| JP | 2017073773 A | 4/2017 |
| KR | 20160129752 A | 11/2016 |

OTHER PUBLICATIONS

Strauss, D., J.; et al.: Toward a taxonomic model of attention in effort fulllistening. In: Cogn Affect Behav Neurosci, 2017, 809-825.
Hanson, V., et al.: Towards a Brain-Machine-System for Auditory Scene Analysis. In: Wearable Electronic Sensors, 2015, 299-320.
Bernarding, C. et al: : Neurodynamic evaluation of hearing aid features using EEG correlates of listening effort. In: Cogn Neurodyn, 2017, 203-215.
Bernarding, C. et al: Objective Assessment of Listening Effort: Effect of an Increased Task Demand. In: IEEE, 2016, 3684-3687.

* cited by examiner

METHOD FOR OPERATING A HEARING AID AND HEARING AID

CROSS-REFERENCE TO RELATED APPLICATION

This application claims the priority, under 35 U.S.C. § 119, of German application DE 10 2017 214 163.8, filed Aug. 14, 2017; the prior application is herewith incorporated by reference in its entirety.

BACKGROUND OF THE INVENTION

Field of the Invention

The invention relates to a method for operating a hearing aid and to a corresponding hearing aid.

In general, a hearing aid serves to reproduce a sound signal in the direction of an ear of a user. To this end, the hearing aid is worn in or on the ear and it has a receiver by which a sound is output. Specifically, a hearing aid serves to take care of a user who is hard of hearing. Usually, such a hearing aid has a number of microphones for recording sound signals from the surroundings and a signal processing unit which suitably modifies, in particular amplifies, the recorded sound signals and then forwards these to the receiver for output.

The use of such a hearing aid for the user depends substantially on the capability of the hearing aid to output the sound signals in such a way that these correspond to the requirements of the user as ideally as possible in a specific situation. This is affected by way of setting a number of operational parameters of the hearing aid, which then define the behavior thereof during operation.

In general, a certain amount of effort is required for perceiving sound signals. This effort is also referred to as listening effort. Here, the listening effort is greater in, e.g., surroundings which contain a multiplicity of competing sound sources and lesser in, e.g., quiet surroundings. A definition for the listening effort is provided, inter alia, in Bernarding et al., "Neurodynamic Evaluation of Hearing Aid Features Using EEG Correlates of Listening Effort", Cognitive Neurodynamics, 2017, DOI 10.1007/s11571-017-9425-5. Therein, the listening effort is defined as a mental effort of the user to process sound signals, i.e. auditory stimuli, particularly in difficult surroundings, i.e. in surroundings with interfering influences or with a multiplicity of sound signals. Thus, this is not a reflex-like action but an effort that is actively wanted and undertaken by the user. This results in an ongoing and oscillatory activity, more precisely an EEG activity.

In comparison with persons with normal hearing, persons who are hard of hearing sometimes require a significantly higher listening effort in the same situation, and so tiring occurs earlier. In certain circumstances, the person who is hard of hearing even attempts to bypass or avoid situations with increased listening effort, which may lead to a reduction in social activities and, ultimately, to a reduced quality of life. Therefore, it is a goal worth pursuing to supply persons who are hard of hearing or persons who merely have impaired hearing with a hearing aid such that the listening effort is minimized.

Published European patent application EP 2 357 851 A1, corresponding to U.S. Pat. No. 8,559,645, has described a method in which the listening effort in certain training situations is initially established by an electroencephalogram, abbreviated EEG. Then, attempts are made to minimize the listening effort by adapting the hearing aid parameters. Here, a value, which then serves as a measure for the listening effort, is derived from the EEG. In Bernarding et al. (loc. cit.), too, a value for the listening effort is derived from an EEG. Therein, hearing aids were operated in different modes of operation and the listening effort was established in each case for these modes of operation; see, therein, page 3, section "Hearing aid fitting" and FIG. 3 on page 8.

SUMMARY OF THE INVENTION

Against this background, it is an object of the invention to specify an improved method for operating a hearing aid and a corresponding hearing aid. Here, the listening effort of a user of the hearing aid should be reduced as strongly as possible.

According to the invention, the object is achieved by a method having the features as claimed in the main method claim and by a hearing aid having the features of the main device claim. Advantageous configurations, developments and variants are the subject matter of the dependent claims. Here, the explanations in conjunction with the method apply analogously to the hearing aid as well, and vice versa.

The method serves to operate a hearing aid. The hearing aid is embodied to be used by a user. Within the scope of the method, a neuronal signal of the user is measured and a listening effort of the user is established therefrom. In the process, both an intensity of the listening effort and a hearing direction are established, in particular exclusively, from the neuronal signal. The intensity and the hearing direction form a hearing vector, wherein the intensity corresponds to a length of the hearing vector and the hearing direction corresponds to an orientation of the hearing vector. The hearing vector is also referred to as listening-effort vector. Depending on the hearing direction specifically and the hearing vector in general, a mode of operation of the hearing aid is then adapted or set for the purposes of reducing the intensity of the listing effort. Thus, the current mode of operation is adapted or there is a switch over into another mode of operation, depending on the listening effort.

A substantial advantage of the invention consists, in particular, of it not only being the intensity of the listening effort that is determined, but also the hearing direction, i.e. the direction in which the user wishes to hear. This hearing direction is used to optimize the operation of the hearing aid. This is because the neuronal signal contains the intention of the user, and so the will of the user can be and, moreover, is extracted from the hearing vector. This will is expressed, firstly, in the intensity which specifies an interest of the user to hear something specific and, secondly, in the hearing direction, too, the latter specifying to where the interest of the user is directed. The will or, more precisely, the hearing will or the hearing interest is thus determined more precisely by determining the hearing direction. Knowledge of the hearing direction then facilitates a significantly more target-directed and needs-based setting of the hearing aid. Then, an ideal mode of operation is found for a given situation, in which the user is situated, and so the listening effort, more precisely the intensity thereof, is advantageously reduced. This unburdens the user and leads to an increase in the quality of life overall.

A central concept, in particular, is to establish the listening effort not as a pure scalar, as in published, European application EP 2 357 851 A1 or as in Bernarding et al. (loc. cit.), which only specifies an intensity of the listening effort but, in contrast thereto, to represent the listening effort as a vector-based object, namely as a vector which, in addition to the information about the intensity of the listening effort, also contains information in respect of the direction of the listing effort. Then, this vector is a hearing vector, which specifies the direction in which and the effort with which the user of the hearing aid hears. While the length of the hearing vector is a measure for the effort with which the user attempts to hear, the orientation of the hearing vector is a measure for the direction in which the user wishes to hear. Here, the hearing vector is derived, in particular, exclusively, i.e. only, from the neuronal signal and precisely not from a signal, such as, e.g., a sound signal, that is external to the user.

In the present case, measuring the neuronal signal measures, in particular, an ongoing or oscillatory activity of the brain of the user in a targeted manner. Accordingly, the neuronal signal is precisely not a result of a specific stimulus and not an event-related signal or else event-related potential. This is because such a specific stimulus produces precisely no neuronal signal from which a hearing intention can be gathered, but only a reflex-like reaction to a specific stimulus, i.e. an event-related signal. Using event-related signals as a result of specific stimuli is described in, e.g., Hanson, Odame, "Towards a Brain-Machine System for Auditory Scene Analysis", 2015, Wearable Electronic Sensors, page 299ff., DOI: 10.1007/978-3-319-18191-2_13. Then, a signal relates to a specific stimulus; by contrast, the ongoing or oscillatory activity, i.e. an ongoing or oscillatory potential, is measured within the scope of the present application, the potential, in particular, not being produced by specific stimuli but containing a specific hearing intention of the user.

In the present case, moreover, both the intensity of the listening effort and a hearing direction, i.e. in summary the listening effort, are determined, in particular exclusively, from the neuronal signal. Advantageously, additional measurements of external signals, in particular, are not necessary and are therefore expediently not carried out either for determining the listening effort. In particular, an additional microphone analysis for the purposes of processing the neuronal signal is dispensed with. The subject matter of the present application therefore is in contrast to the method described in, e.g., O'Sullivan et al., "Neural Decoding of Attentional Selection in Multi-Speaker Environments Without Access to Clean Sources", 2017, Journal of Neural Engineering, DOI: 10.1088/1741-2552/aa7ab4, in which a microphone analysis is carried out to evaluate a measured EEG signal. Here, knowledge that the EEG signal follows the envelope of the tracked sound source is used to solve the cocktail-party problem; however, this does not correspond to establishing a hearing intention, and therefore this does not correspond to determining the listening effort either. In particular, the listening effort is an external/perceptual listening effort, i.e. a listening effort that is directed to external objects, e.g. specific sound sources in the surroundings, in contrast to an internal listening effort, which is directed to internal objects, such as, e.g., the interpretation or understanding of specific expressions or languages. A definition of external and internal listening effort is provided in Strauss and Francis, "Toward a Taxonomic Model of Attention in Effortful Listening", Cognitive, Affective & Behavioral Neuroscience, 2017, DOI: 10.3758/s13415-017-0513-0. There, the listening effort is represented as a vector in the two-dimensional space of the internal and external listening effort, i.e. the orientation of the vector therein specifies a ratio of the internal to the external listening effort, with, by contrast, the hearing direction remaining unconsidered. As an alternative or in addition to the external listening effort, the internal listening effort is also established and used for adapting or setting the mode of operation in a profitable manner.

Within the scope of the method, attempts are made to set the hearing aid in such a way that the intensity of the listening effort is reduced. To this end, the mode of operation is set or adapted depending on the hearing vector. Expressed differently: the established hearing direction is used as additional information for reducing the listening effort. Each mode of operation is defined by specific values for a number of operating parameters of the hearing aid. By way of example, such operating parameters are a gain factor, a compression factor, a filter bandwidth or the like. Reducing the listening effort, i.e. reducing the intensity, is brought about by adapting the operating parameters of the hearing aid. Here, either adaptation is brought about within the scope of a certain mode of operation, which is then adapted, or the operating parameters are adapted in such a way that even a different mode of operation is set. The additional knowledge of the hearing direction now allows these operating parameters to be set in a much more targeted manner. Here, the hearing direction is incorporated into the reduction concept in a targeted manner instead of a general attempt being made merely to reduce the intensity of the listening effort. With the orientation, the hearing vector contains a measure of the intention, more precisely the hearing intention, of the user. Thus, the hearing intention of the user is encoded in the hearing vector. Knowledge about the desired hearing direction then facilitates a reduction of the parameter space in which attempts are made to minimize the intensity of the listening effort by suitable choice of the operating parameters.

The mode of operation is preferably adapted by virtue of adapting a number of operating parameters of the hearing aid by a closed-loop control, wherein the operating parameters are used as manipulated variables and wherein the intensity of the listening effort is used as a controlled variable. The purpose of the closed-loop control lies in minimizing the intensity of the listening effort. Thus, the operating parameters are adapted until the intensity assumes a minimum value. Suitably, the closed-loop control is part of a control unit of the hearing aid. However, alternatively, outsourcing of the closed-loop control is also expedient. The closed-loop control is then implemented on an external appliance, as a result of which computational power of the hearing aid is saved. The closed-loop control explicitly takes account of the hearing direction; i.e. knowledge of the hearing direction is incorporated into the closed-loop control. Here, in particular, the hearing direction is neither a controlled variable nor a manipulated variable since the hearing direction, as hearing intention of the user, is not adjustable by the hearing aid. However, the hearing direction advantageously serves as a target variable for the setting or adaptation of the operating parameters, namely preferably in such a way that this simplifies hearing in the hearing direction. By taking account of the hearing direction, the closed-loop control is more effective overall because an additional boundary condition or target condition is present with the hearing direction, simplifying an ideal setting of the operating parameters.

Knowledge of the intended hearing direction of the user is very particularly suitable for adapting the mode of operation with respect to a directional characteristic of the hearing aid. In a preferred configuration, the mode of operation is then a directional hearing operation, in which sound signals are output amplified from a preferred direction relative to sound signals from other directions. The directional hearing operation is then adapted by virtue of the hearing direction being set as the preferred direction. Without knowledge of the hearing direction, the latter would have to be estimated on the basis of other information, e.g. by way of a microphone analysis or by way of acceleration sensors or the like. However, such methods are based for design reasons only on external information, that is to say there always remains an uncertainty as to whether the set preferred direction is actually the direction that is wanted by the user. By contrast, the hearing intention of the user is contained for design reasons in the hearing vector. The hearing direction actually wanted is established directly by the measurement and evaluation of the neuronal signal, because the neuronal signals result precisely in dependence on the hearing direction that is wanted by the user. The selection of the preferred direction during directional hearing is consequently significantly less susceptible to errors.

Expediently, the above-described adaptation of the directional hearing operation is combined with the closed-loop control described further above. Then, the hearing direction is suitably a reference variable in an open-loop control or closed-loop control for one of the operating parameters, in particular the preferred direction during the directional hearing operation. The intensity of the listening effort is then minimized particularly advantageously by way of a closed-loop control by virtue of the hearing direction being set as the preferred direction for the directional hearing. This is based on the consideration of simplifying, in a targeted manner, hearing in the hearing direction that is wanted and actively sought after by the user.

The directional characteristic emerges in the hearing aid from, in particular, specific processing of microphone signals of the hearing aid. Expressed differently: the hearing aid has, in particular, a number of microphones that each produce a microphone signal during operation and the microphone signals are modified by means of a control unit, in particular combined with one another, in such a way that sound signals from the preferred direction are amplified in relation to other sound signals. In the present case, the microphone signals are now processed depending on the hearing direction.

During directional hearing, a directional lobe, in particular, is formed, the latter having a directional angle and a width, the directional angle and the width depending, in detail, on the processing of the microphone signals in particular. The directional angle, i.e. the alignment of the directional lobe, and the width are adaptable within the scope of the directional hearing operation, and so even the directional hearing operation is adaptable in this respect and it is adapted in that case by virtue of the directional angle or the width or both being adapted depending on the hearing vector. Specifically, the directional angle is expediently set in such a way that the directional lobe points in the hearing direction.

However, determining the hearing direction is not only advantageous when aligning the directional lobe; it is also advantageous for determining whether directional hearing is even desired, i.e. whether the directional hearing operation should even be set. In an advantageous configuration, the mode of operation then is an omnidirectional hearing operation, which is set if establishing the hearing direction fails. Should the user not desire to listen in a certain direction, determining the hearing direction will necessarily fail and no hearing direction can be established. In this respect, this identifies the desire of the user for omnidirectional hearing, i.e. unfocused hearing in all directions. In this case, the omnidirectional hearing operation, in which no preferred direction is set but in which, in particular, sound signals from all directions are equally output to the user, is then set.

It is also conceivable that the user may not want the omnidirectional hearing operation but that establishing the hearing direction fails on account of other circumstances or faults, for example in the case of incorrect positioning of the hearing aid in such a way that the measurement of the neuronal signal is faulty. Here too, the omnidirectional hearing operation then is advantageous, for example for safety reasons.

In a suitable configuration, the hearing vector is assigned on the basis of the hearing direction to one of five directional classes, namely "front", "back", "left", "right" or "unfocused", and each of these directional classes has assigned to it a mode of operation, namely "directional hearing to the front", "directional hearing to the back", "directional hearing to the left", "directional hearing to the right" or "omnidirectional hearing", and the mode of operation which is assigned to the directional class to which the hearing vector belongs is set. The reduction to the five aforementioned classes significantly simplifies the adaptation or setting of the mode of operation. Moreover, a correspondingly large tolerance range is provided by this simplification for establishing the listening effort and, specifically, the hearing direction, and so a sufficiently suitable mode of operation is nevertheless reliably set, even in the case of an imprecise determination of the listening effort.

A two-dimensional hearing vector, i.e. a hearing vector that lies in only one plane, is already suitable for applying the hearing vector in a hearing aid. This plane is a hearing plane of the user and extends horizontally such that the hearing direction is correspondingly restricted to the left, right, front and back. However, in an advantageous configuration, the hearing vector is three-dimensional and consequently describes a hearing direction in a hearing space. Using such a hearing vector, it is possible in a suitable configuration to map the directions up and down as well in addition to the above-described directions of left, right, front, back and unfocused.

In a particularly preferred configuration, the hearing vector is not mapped discretely onto the aforementioned few directions but instead established with a high resolution. Expressed differently, a three-dimensional space around the user is segmented into a plurality of directions, wherein each direction corresponds to a solid angle in the three-dimensional space and wherein each direction has assigned to it a mode of operation for hearing in the respective direction, i.e. for the preferred output of sound signals from the associated solid angle. Consequently, the hearing vector is represented continuously over the three-dimensional space such that a particularly high directional resolution is obtained. Using this, the mode of operation which is assigned to the direction corresponding to the hearing vector is then set. A segmentation of the space and representation of the hearing vector is thus not restricted to the six spatial directions of left, right, front, back, up and down, but instead it has a significantly finer resolution. In the above-described coarse resolution with the six specific directions, the three-dimensional space is divided into six solid angles. By contrast, in the high-resolution segmentation, the three-dimensional space is divided into significantly more than six solid angles, preferably at least into 100 solid angles. In the case of directional hearing, in particular as described above, the preferred direction is then set precisely in the hearing direction and not only mapped approximately to a restricted number of directional classes.

However, knowledge of the hearing direction is not only advantageous when adapting or setting a directional hearing operation but, very generally, also for adapting any algorithm that controls the hearing aid. Preferably, the mode of operation is therefore adapted by virtue of a noise reduction, a gain, a compression, an audio streaming, a tinnitus algorithm or an own-voice recognition being adapted, in particular depending on the hearing direction. The list of algorithms above is not complete; however, the aforementioned algorithms are adapted particularly preferably. The response of a respective algorithm is determined by one or more of the operating parameters of the hearing aid. In this respect, adapting the operating parameters typically also adapts an algorithm dependent thereon. A respective algorithm serves to carry out signal processing, in particular within the hearing aid, and it determines how the microphone signals are modified and finally output. Here, a respective algorithm is advantageously adapted in such a way that the intensity of the listening effort is reduced.

The gain then determines, in particular, how the microphone signals are amplified and, in general, how an input signal is amplified. The gain is preferably frequency-dependent. The gain is preferably adapted within the scope of directional hearing, specifically in such a way that the signals from the preferred direction are amplified more strongly. Generally, the gain for reducing the intensity of the listening effort is expediently increased, but advantageously only for sound signals from the hearing direction.

In the case of audio streaming, a signal source is selected by an audio streaming algorithm. By way of example, the hearing aid has as signal sources a microphone or microphone array, a data transfer interface, a telecoil and an audio interface or a subset thereof. The audio streaming algorithm now selects one of these signal sources for output to the user. Knowing the hearing direction now allows an improved selection. By way of example, the user is listening to music via the audio interface when the user is approached by a conversation partner, for example, to whom the user now wishes to listen. This intention is then identified by virtue of the hearing direction, which points in the direction of the conversation partner, being established. The audio streaming is then adapted by virtue of the microphone being selected as the signal source and by virtue of the audio interface, in particular, being deactivated. By way of example, adapting the audio streaming contributes to reducing the intensity of the listening effort by virtue of selecting that signal source for which the intensity is minimized from a plurality of signal sources.

By way of example, the tinnitus algorithm is a tinnitus masker or a so-called tinnitus noiser. Typically, the tinnitus algorithm modifies an input signal in such a way that, in a tinnitus frequency range, the input signal is filtered, i.e. attenuated, or that an additional signal, e.g. a noise signal, is added to the input signal.

For the purposes of reducing the intensity of the listening effort, the own-voice recognition is expediently also adapted. The own-voice recognition recognizes the own voice of the user and filters the latter out of the input signal. As a result, the user can better understand other sound signals.

When reducing the intensity of the listening effort, there is, in principle, the possibility of the latter not being completely eliminated and a residue of intensity remaining such that the user must continue to exert effort for listening. In an advantageous configuration, the mode of operation is adapted or set and, in the process or thereafter, a notification is output to the user should the intensity not drop below a lower intensity limit value. This is based on the consideration that a reduction to an intensity above the lower intensity limit value continues to require great effort, which may lead to corresponding tiring or irritation of the user. Therefore, a notification that the setting or adaptation of the mode of operation cannot be optimized any further is output to the user. The user can then make a decision as to how to proceed. In an expedient variant, the notification comprises the suggestion of changing the surroundings or the situation, for example move into a quieter region, set background music or a television to be quieter or pause a phone call. The notification and, specifically, the suggestion as well are referred to, in particular, as counseling. A basic idea here lies in providing the user with notifications and suggestions which contribute to a further reduction in the intensity of the listening effort but which do not lie within the sphere of influence of the hearing aid.

In particular, adapting or setting the mode of operation on the basis of the listening effort is carried out automatically. However, expediently, the selected adaptation or setting is preventable and it is also then prevented and, as it were, overwritten. The described intention-caused, i.e. intention-dependent, adaptation or setting of the mode of operation is therefore ignored. This is based on the consideration that it is more advantageous in certain situations to deviate from the hearing intention of the user and, instead, apply a deviating adaptation or setting.

In a suitable configuration, adapting or setting of the mode of operation is preventable by manual input by the user and it is also prevented by such a manual input. This allows the user to overwrite the result of the automatic recognition of the listening effort and the adaptation or the setting dependent thereon.

As an alternative or in addition thereto, the adaptation or setting of the mode of operation is prevented should a certain key situation be present, the key situation being distinguished by a key stimulus to which the hearing intention of the user is initially not directed but nevertheless is important to the user and therefore should be output to the user despite a lack of hearing intention. Accordingly, if a key situation is present, the key stimulus is output to the user irrespective of the listening effort, in particular the hearing direction, and, in particular, irrespective of the hearing intention, and this prevents an inadvertent suppression within the scope of the regular adaptation or setting. As a result, important sound signals are forwarded to the user in unimpeded fashion. Key stimuli are, for example, the noise of an approaching vehicle or warning signals from the surroundings, such as sirens, for example, or else announcements. Such key stimuli are relevant to the user irrespective of their current hearing intention and should not be suppressed where possible. Corresponding key situations are then, for example, crossing the road, an emergency situation or waiting at a station platform. The key situation or the key stimulus or both are recognized, for example, by an additional sensor or by means of a microphone analysis.

In a preferred configuration, the listening effort is established by an EEG, in which the neuronal signal is measured by means of an electrode array. The electrode array has a number of contacts or else measurement contacts that are arranged at the head of the user and that produce an EEG signal, from which the hearing vector is determined. In the present case, the contacts are also referred to as electrodes in each case. The neuronal signals are bioelectric signals and, in particular, brain waves of the user. The contacts of the electrode array are individual electric contacts or poles in each case, which are applied to the head of the user, e.g.

on the scalp. Then, a potential difference is measured between respectively two contacts, the potential difference being forwarded to an evaluation unit as a sensor signal. The electrode array thus has a multi-polar embodiment in order to measure the sensor signal as a potential difference between two individual contacts at different positions on the head of the user. Accordingly, in the case of more than two contacts, correspondingly more sensor signals, which are forwarded to the evaluation unit, are also produced.

In one variant, the evaluation unit is part of the control unit. In a particularly advantageous variant, the evaluation unit is an external evaluation unit and part of an external appliance such that the evaluation is carried out outside of the hearing aid and computational power in the hearing aid is saved in this way. By way of example, the external appliance is a smartphone or a computer of the user, or a server.

In particular, the evaluation is implemented by means of a mathematical preparation of the measured neuronal signal. In a suitable configuration, the phase of each individual sensor signal is extracted to this end and the distribution of these phases then is examined by virtue of a focus of the distribution being formed. This focus and, in general, the arrangement of the phases (phase clustering) in a certain situation are then used to evaluate the neuronal signal and determine the hearing vector. Preferably, the preparation is carried out as described in the section "Data analysis" in Bernarding et al. (loc. cit.).

The electrode array has at least a bipolar embodiment, i.e. has at least two contacts between which a potential difference is then measured, for the purposes of producing the sensor signal. In principle, an electrode array with more than two contacts is also suitable. For EEG measurements in neuropsychological research or in clinical surroundings, use is made of, e.g., 32 or even 128 contacts, which are arranged distributed over the entire head. Then, one of the contacts is expediently used as a reference contact, which provides a reference potential against which a measurement is carried out with the other contacts, in each case in a bipolar arrangement. Particularly preferably, a configuration is such that the electrode array has exactly one measurement contact and one reference contact, i.e. only two contacts in total, which are both integrated into the housing of the hearing aid and consequently are arranged particularly close to the ear of the user in each case.

In a suitable configuration, the EEG signal is a signal pattern and the hearing vector is determined by virtue of the measured signal pattern being compared to a number of signal patterns known in advance. In particular, the signal pattern is a spatial signal pattern, which emerges from the configuration of the electrode array and, specifically, the arrangement of the contacts. Each contact measures at a specific position on the head, and so the measurement values of the contacts are assigned to precisely those positions and the measurement values are spatially distributed as a result thereof and form the signal pattern. By way of example, the signal pattern is composed of the phases described further above; i.e. the signal pattern is a matrix, which contains the phases as entries, or, in general, the preferably prepared sensor signals of the contacts. The signal pattern is then compared to signal patterns known in advance, for which the hearing vector is known in each case. By way of example, the comparison is a simple image comparison, in which the signal patterns are compared to one another as images. By way of example, the signal distributions known in advance are determined in a training method or in a fitting session. As an alternative or in addition thereto, the signal patterns known in advance are obtained by way of an external database.

In the present case, the electrode array has an embodiment that is as compact as possible. To this end, the electrode array, in a suitable configuration, is only arranged in the region of the ear of the user, more precisely in the region of the auricle. Expressed differently, the electrode array is preferably arranged at a distance from the ear of at most 5 cm, particularly preferably of at most 2 cm therefrom. This ensures that the electrode array is only distributed over a small part of the head of the user and, as a result thereof, is particularly suitable for daily use.

In a preferred configuration, the electrode array only has at most five contacts, particularly preferably exactly two contacts. Such a restriction in the number of contacts also contributes to the compactness of the electrode array and to the suitability of the hearing aid and of the method for daily use. The reduction in the number of contacts, particularly in comparison with clinical surroundings, is based on the observation that, in particular, a restricted number of contacts completely suffices for a sufficiently accurate determination of the hearing vector. An advantageous reduction in the number of contacts and a simplified measurement of the neuronal signal are possible and therefore advantageously also carried out, particularly in conjunction with the above-described classification of the hearing vector into a few classes and, in particular, into only five classes. Since the requirements on the accuracy are correspondingly low on account of the only coarse classification, there is also no need to measure the neuronal signal particularly accurately, and so, expediently, use is then made of a correspondingly compact electrode array, which only has a few contacts.

The contacts of the electrode array are preferably embodied as external contacts in each case, i.e. as contacts which are arranged outside of the head of the user. Alternatively, a configuration of one or more of the contacts as implants is also suitable. As already indicated above, a respective contact is preferably integrated into a housing of the hearing aid. In particular, this also facilitates an EEG measurement not only within the scope of a fitting session at an audiologist using complicated apparatuses but in an unnoticed and invisible manner during daily use as well, i.e. during the normal operation of the hearing aid. However, a configuration as a separate electrode array, which is then connected to the hearing aid, in particular, via a signal line or wirelessly, is also suitable.

Preferably, the neuronal signal is measured at the auditory cortex of the user, i.e., in particular, at least in the vicinity of the auditory cortex. A measurement of the neuronal signal at the mastoid, i.e. at the mastoid part of the temporal bone, is particularly suitable since the auditory cortex lies in the direct vicinity of the mastoid and, at the same time, the associated contact is attached close to the ear and can consequently be worn largely unnoticed. Examinations have shown that the hearing direction is already at least approximately determinable with a single contact in the vicinity of the auditory cortex. However, a plurality of contacts leads to results that are more accurate.

In principle, the neuronal signal can be measured only on one side and can also be used in this form to determine the hearing vector. However, a configuration is preferred in which the neuronal signal is measured on both sides of the head of the user, in particular as described above, in the vicinity of the auditory cortex in each case. In the process, a right measurement value and a left measurement value are produced and the hearing direction is then determined by comparing the right measurement value and the left measurement value. In a first variant, at least two potential differences are measured to this end by virtue of the two contacts being measured against a reference contact in each case or against a single, common reference contact. The two measurement values then emerge in each case as a potential difference in relation to a reference contact. In another variant, the two measurement values each emerge as a signal at one of the contacts and the measurement values are directly compared to one another such that a separate reference contact is dispensed with. By way of example, the difference or the ratio of the two measurement values is formed.

In a particularly preferred configuration, the intensity of the listening effort is determined on both sides of the head of the user in a manner that is similar to the aforementioned method with the left and right measurement value, and so a left intensity and a right intensity are measured and the hearing direction is determined from the intensities. This is based on the discovery that the intensity of the listening effort is different on the two sides of the head depending on the position of a sound source and that thus the hearing direction can be established, and therefore preferably also is established, by a comparison of the left and the right intensity by way of a measurement of a respective neuronal signal on both sides. Accordingly, a lateralization, i.e. a spatial dependence of the intensity, from which the hearing direction is derived, is established, in general, by determining the intensity at different positions on the head. Expediently, the two-sided measurement occurs in a binaural hearing aid, in which each of the individual appliances initially measures the intensity of the listening effort on one side, in particular independently of the other individual appliance. Then, the two intensities are brought together and compared in a control unit in one of the individual appliances or on an external appliance, the difference or the ratio of the two intensities, for example, being formed.

In a particularly preferred configuration, the hearing aid is a binaural hearing aid and has two individual appliances that are to be worn on different sides of the head of the user. However, in principle, a mono-aural hearing aid with only one individual appliance for taking care of only one ear of the user is also suitable. Then, each of the individual appliances expediently has a corresponding electrode array for measuring the neuronal signal on the respective side. As an alternative to the separate measurement by means of two electrode arrays, the two individual appliances use a single electrode array together. Expediently, the hearing vector is determined by virtue of the neuronal signals of both sides being evaluated together. However, in principle, a configuration in which the hearing vector is initially established redundantly by both individual appliances and then the two hearing vectors are compared to one another or averaged in order to determine a single hearing vector is also suitable.

In an expedient configuration, the mode of operation is adapted or set on the basis of an evaluation of a sensor signal of an additional sensor, wherein the sensor signal is classified by virtue of the hearing direction being used as an additional feature. This is based on the consideration that the evaluation of various additional sensors of the hearing aid also profits from the additional knowledge of the hearing vector and, specifically, the hearing direction. Usually, sensor signals are classified by a control unit in order to obtain information in respect of the surroundings or the current situation from the sensor signal. The classification is brought about on the basis of features that are sought after in the sensor signal. Here, a plurality of sensor signals of a plurality of additional sensors can also be examined together in an appropriate manner. The result and the correctness thereof are decisively dependent on the recognizability and distinguishability of the features in order to carry out a classification that is as error-free as possible. Now, the hearing vector provides additional features, namely the intensity of the listening effort and the hearing direction, which facilitate a more accurate classification in combination with the sensor signal. By way of example, the additional sensor is a microphone or an acceleration sensor or the like.

Preferably, setting or adapting the mode of operation is carried out within the scope of an optimization and a mode of operation, which was adapted or set in this manner for the purposes of reducing the intensity of the listening effort, is stored as an optimized mode of operation; in short, the adaptation or setting is stored. Then, the optimized mode of operation is automatically set again, selected or established if the same situation, or at least a similar situation, occurs again, i.e. if, in particular, the same hearing vector which was the original reason for the optimization occurs again. In this way, a measurement of the neuronal signal and a corresponding evaluation are advantageously initially dispensed with in known situations; instead, the already carried out and stored optimization is resorted to. By way of example, this is brought about within the scope of a fitting session or in a training method. In a suitable variant, the optimization is undertaken by the user themselves, for example by means of a special training program.

A user-specific optimization is carried out in a suitable configuration, i.e. the mode of operation is optimized in a user-specific manner. Here, a mode of operation is found for a given hearing direction, said mode of operation minimizing the intensity of the listening effort for the user. This mode of operation then is a mode of operation that is specific to, and individually optimized in respect of, the user. This mode of operation is stored and set again should the same hearing direction be established again. Thus, overall, an optimized mode of operation that is adapted to the user is found for each hearing direction, in particular.

In a further suitable configuration, a situation-specific optimization is carried out, i.e. the mode of operation is optimized in a situation-specific manner, i.e., in particular, in a surroundings-specific manner, too. The hearing vector is established in a given ambient situation and a mode of operation is determined, said mode of operation minimizing the intensity of the listening effort in the given ambient situation. This mode of operation is then set again in the case of a repeated identification of the ambient situation. Then, the current ambient situation, abbreviated to situation, is initially determined during the operation of the hearing aid, for example by means of an additional sensor or within the scope of a microphone analysis; then, the mode of operation already optimized for this ambient situation is set if such a mode of operation had already been established. By way of example, an ambient situation is a concert or a cocktail party or a conversation with a counterpart, or the like.

A combination of the two aforementioned configurations is also particularly expedient such that, then, there is a user-specific and then, at the same time, situation-specific optimization and then, should a certain hearing direction be identified in a specific situation again, the mode of operation optimized therefor is set.

Moreover, a data interchange, in which the results of the optimization and, in general, the adaptation or setting of the mode of operation for a user are made available to other users, too, is advantageous. To this end, the adapted or set mode of operation is transmitted together with additional information to an external database and thus made available for use by other users.

In an expedient configuration, the user belongs to a class of users. By way of example, the different users are classified into classes according to the type of damage to the hearing, age, hearing habits or similar parameters. Then, a mode of operation is determined in a given ambient situation, the mode of operation minimizing the intensity of the listening effort, and this mode of operation is stored in an external database in order to be set in the case of another user of the same class or in the same ambient situation or in the case of both.

Conversely, the user belongs to a class of users and, in a suitable configuration, the hearing aid is set in a given ambient situation by virtue of a mode of operation for precisely this class of users or for precisely this ambient situation or for both being taken from the external database and being used as a starting point for minimizing the intensity. Accordingly, the hearing aid retrieves the optimization results for similar users or for similar ambient situations or for both from the external database and proposes the use thereof to the user. Then, the optimization results also serve as a starting point for a further optimization, in particular a user-specific optimization. In this context, an evaluation system is also advantageous, the user evaluating a mode of operation downloaded from the external database in said evaluation system such that, in future, a mode of operation with a better evaluation is more likely to be proposed to other users, for example on account of their class.

Preferably, the hearing aid is a so-called BTE aid, which is worn behind the ear. This includes so-called RIC aids, in which the receiver is inserted into the auditory canal, but the remaining hearing aid is worn outside thereof. However, in principle, other designs such as ITO (in the ear) or CIC (completely in the auditory canal) for example are also suitable. However, the invention is not restricted to a hearing aid for caring for a person who is hard of hearing. In a likewise suitable configuration, the hearing aid is a headset or a similar appliance for sound output. What is essential is that the hearing aid has a receiver for outputting sound.

The listening effort is preferably established continuously during normal operation of the hearing aid, i.e., in particular, during daily use by the user, while the latter wears the hearing aid and uses it normally. Likewise, the mode of operation is adapted or set continuously depending on the hearing vector. Here, in particular, the neuronal signal is measured continuously and, as it were, monitored thereby such that changes are reacted to immediately. In particular, as already described further above, the ongoing or oscillatory activity, in particular the EEG activity, of the user, and precisely not a purely reflex-like or event-related activity, is measured in the process. Accordingly, the listening effort is established and hence monitored within the scope of a background measurement or background monitoring and preferably in an ongoing, i.e. continuous, manner. The method does not only serve for an initial setup of the hearing aid at the audiologist in a fitting session but is carried out precisely during normal operation in order to obtain, continuously and according to needs, an optimization of the mode of operation in respect of the listening effort.

Other features which are considered as characteristic for the invention are set forth in the appended claims.

Although the invention is illustrated and described herein as embodied in a method for operating a hearing aid and a hearing aid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
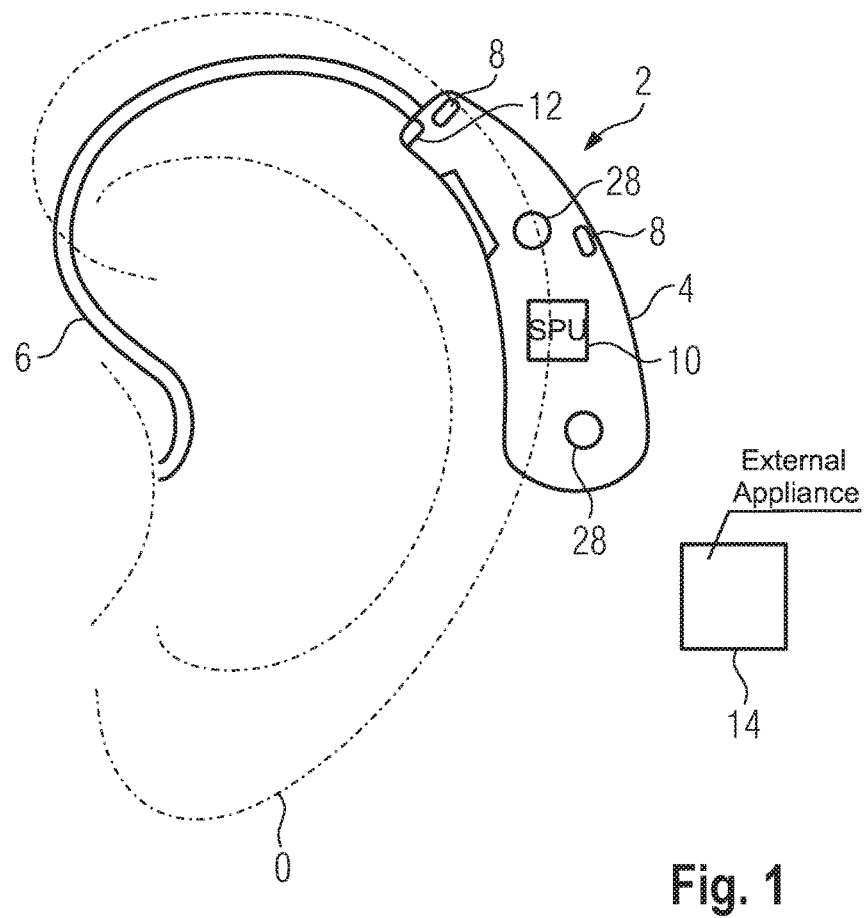
FIG. 1 is an illustration of an ear of a user and a hearing aid.

Referring now to the figures of the drawings in detail and first, particularly to FIG. 1 thereof, there is shown a hearing aid 2, which is worn behind an ear O of a user not illustrated in any more detail. Here, the hearing aid 2 is a BTE hearing aid, which has a housing 4, which is worn behind the ear O and from which a sound tube 6 extends into the auditory canal. Furthermore, the hearing aid 2 has a number of microphones 8, which record sound signals from the surroundings of the user. Then, these sound signals are modified, in particular amplified, by a control unit 10 and then output via a receiver 12. From the receiver 12, the modified sound signals then pass into the ear O via the sound tube 6. For secure hold of the sound tube 6, an earpiece not shown in any more detail is attached at the end side to the latter, the earpiece being inserted into the auditory canal. Furthermore, FIG. 1 shows an external appliance 14, which is a smartphone or a server, for example. The hearing aid 2 and the external appliance 14 are embodied for transferring data between one another, e.g. by wireless communication.

FIG. 1 only shows an individual appliance of a binaural hearing aid 2. Accordingly, the hearing aid 2 has two corresponding individual appliances as shown in FIG. 1, which are then worn accordingly on different sides of the head of the user. However, in one variant, the hearing aid is a mono-aural hearing aid 2 and only has one single appliance.

Figure 2:
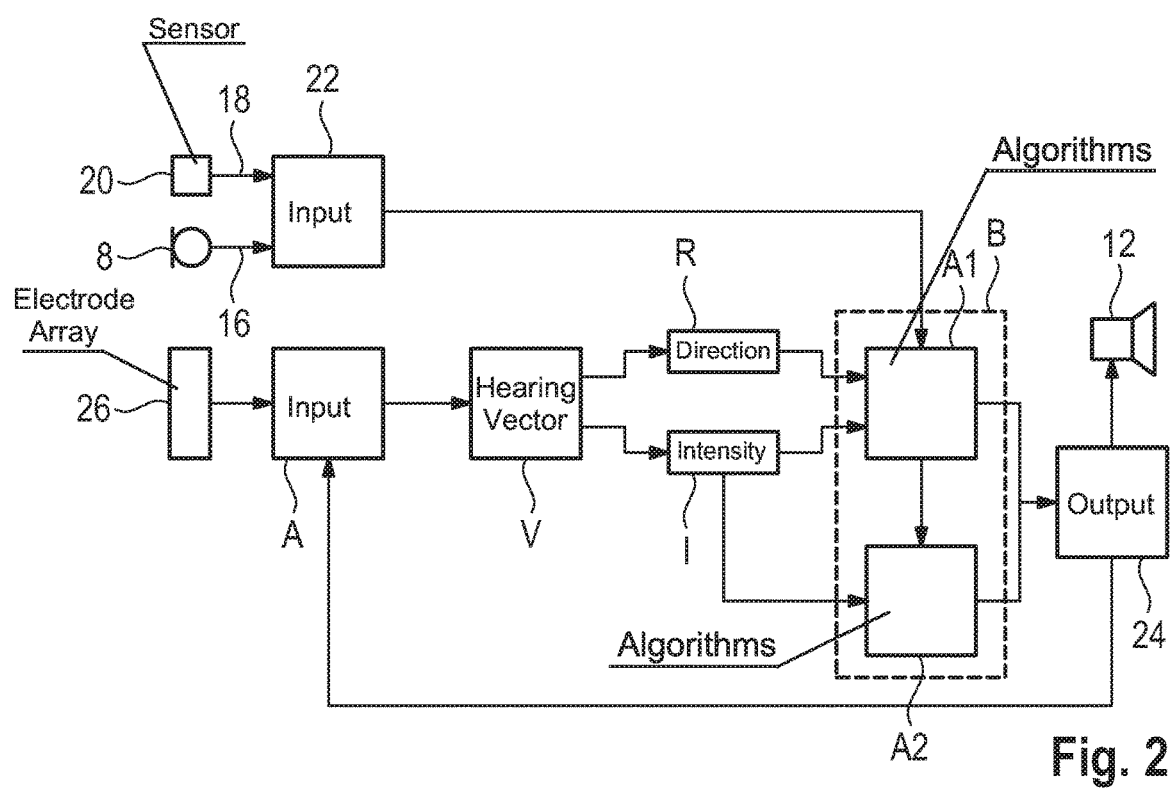
FIG. 2 is a block diagram showing a method for operating the hearing aid.

FIG. 2 shows how a neuronal signal of the user is measured during the operation of the hearing aid 2 and how a listening effort H of the user is established therefrom. Both an intensity I of the listening effort H and a hearing direction R are established from the neuronal signal, wherein the intensity I and the hearing direction R form a hearing vector V and wherein a mode of operation B of the hearing aid 2 is adapted or set depending on the hearing direction R for the purposes of reducing the intensity I of the listening effort H.

Within the scope of the operation of the hearing aid 2, sound signals from the surroundings are initially recorded by the microphones 8 and these sound signals are converted into microphone signals 16. Together with signals 18 of one or more additional sensors 20, these form an input 22. Now, the microphone signals 16 are modified by algorithms A1, A2 and forwarded to an output 24 and output by means of the receiver 12. Accordingly, the modification of the microphone signals 16 depends on the algorithms A1, A2. Together, these form a mode of operation B. The latter is now adapted during operation depending on the hearing vector V and, specifically, the hearing direction R in order to keep the intensity I of the listening effort H as low as possible.

In FIG. 1, the listening effort H is established by an EEG, in which the neuronal signal is measured by an electrode array 26. The electrode array 26 has a number of contacts 28, which are also referred to as measurement contacts or electrodes, which are arranged on the head of the user and which produce an EEG signal, from which the hearing vector V is determined. In the present case, the brain waves of the user are measured as a neuronal signal. The contacts 28 of the electrode array 26 are individual electric contacts or poles in each case, which are attached to the head of the user, for example on the scalp. In FIG. 1, the contacts 28 are integrated into the housing 4 of the hearing aid 2 and then rest close to the ear O on the head of the user. Then, a potential difference is measured between respectively two contacts 28, the potential difference being forwarded to an evaluation unit as a sensor signal. The evaluation unit is either part of the control unit 10 or of the external appliance 14 in this case.

Figure 3:
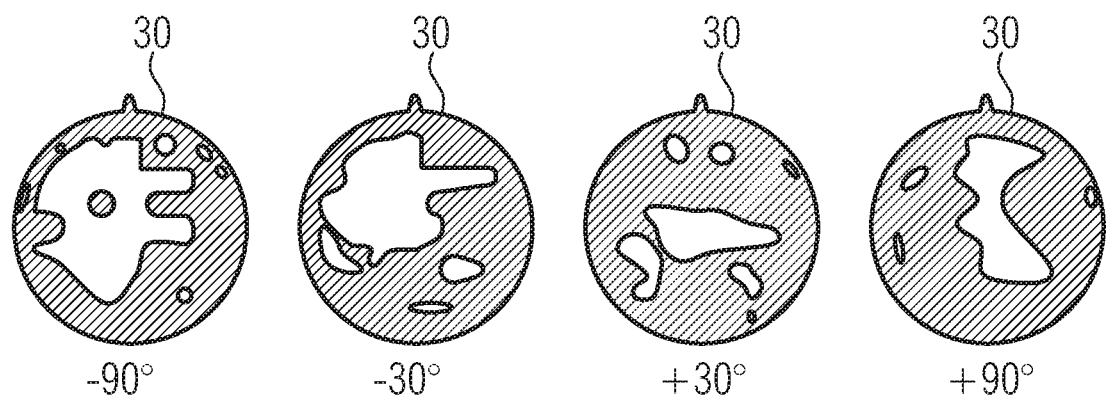
FIG. 3 is an illustration showing a plurality of measurement results of an EEG measurement.

The evaluation is carried out by a mathematical preparation of the measured neuronal signal. FIG. 3 shows, in an exemplary manner, a measurement result that was recorded from an EEG with a multiplicity of contacts 28. The measurement results in each case show the head of the user, as seen from above, with the direction of view being indicated in the figure by a tip at the upper edge of the signal pattern in each case. The phase was extracted from the individual sensor signals of the contacts 28 in each case and then the phases were presented spatially in a signal pattern 30. FIG. 3 shows four different signal patterns 30, which belong to different hearing vectors V. Here, a sound source that the user would like to hear, i.e. in respect of which a hearing intention is present, is situated in each case at a certain angle relative to the median plane of the user. Consequently, the hearing direction R intended, i.e. desired, by the user can be gathered from the signal patterns 30. As viewed from left to right, the angle relative to the median plane is −90°, −30°, +30° and +90°. The differences between the signal patterns 30 are clearly identifiable. Then, the hearing vector V is established by comparison with signal patterns 30 known in advance.

A signal pattern 30 as shown in FIG. 3 is well-suited to determine the hearing vector V on account of the large amount of data; however, it requires many contacts 28. By contrast, particularly few contacts 28 are used in the exemplary embodiment of FIG. 1, namely only two contacts 28 per individual appliance. As a result, the electrode array 26 is only distributed over a small part of the head of the user and particularly suitable for daily use as a result thereof.

Figure 4:
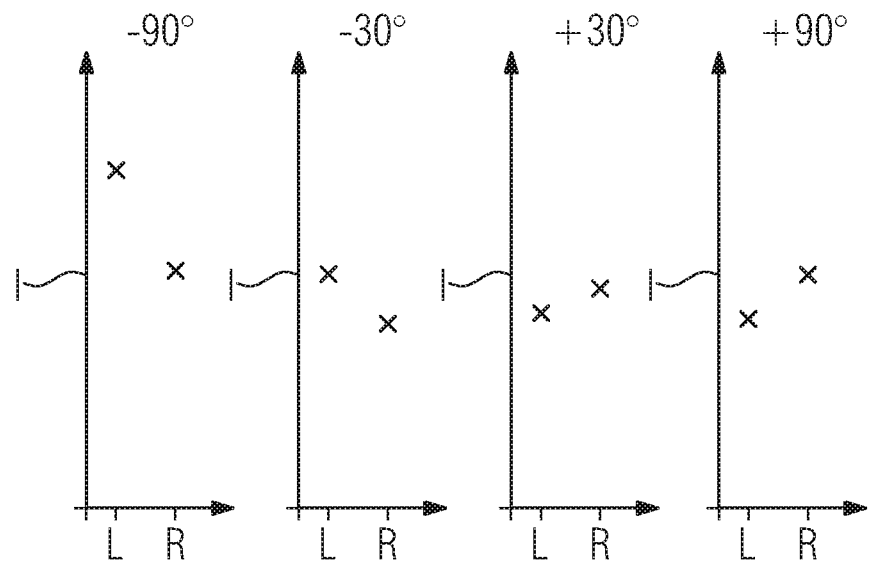
FIG. 4 is a graph showing a plurality of evaluations of measurements of a neuronal signal.

FIG. 4 shows four measurements, in which the neuronal signal was measured in each case on both sides of the head, respectively at the mastoid of the user. The measurement on the left side is denoted by L in each case; the measurement on the right side is denoted by R in each case. The intensity I of the listening effort H is plotted in the vertical direction in each case. Like in FIG. 3, the four measurements differ in terms of the position of a sound source relative to the median plane of the user. From left to right, the sound source is arranged at an angle of −90°, −30°, +30° and +90° relative to the median plane. It is clearly identifiable that the hearing direction R can also be derived from the measurements of the intensity I. Thus, the measurements can be lateralized and can be assigned to a hearing direction R. In general, it is recognizable from FIG. 4 that the intensity I on the side of the sound source is greater than on the opposite side. It is also clear that the hearing direction R can be determined not only qualitatively but also, rather, quantitatively as well. Furthermore, it is also clear from FIG. 4 that already one measurement at the mastoid is sufficient for establishing the hearing direction R, and so a compact electrode array 26, as shown in FIG. 1, already suffices for determining the hearing vector V.

Knowledge of the intended hearing direction R of the user is used in the present case for adapting the mode of operation B in respect of a directional characteristic of the hearing aid 2. Thus, the mode of operation B is a directional hearing operation, in which sound signals from a preferred direction are output in amplified manner relative to sound signals from other directions. Now, the directional hearing operation is adapted by virtue of the hearing direction R being set as the preferred direction. Then, the algorithm A1 is a microphone algorithm, for example, which modifies and mixes the microphone signals 16 of the microphones 8 in such a way that a certain directional characteristic emerges. The latter is defined by a directional lobe, which has a directional angle and a width, wherein the directional angle and the width depend, in detail, on the processing of the microphone signals 16 in particular, i.e. on the algorithm A1. The directional angle, i.e. the alignment of the directional lobe, and the width are then adapted within the scope of the directional hearing operation by virtue of adapting the algorithm A1 and consequently the mode of operation B such that, as a result, the directional angle or the width or both is/are adapted depending on the hearing vector V, more precisely such that the directional angle is set in such a way that the directional lobe points in the hearing direction R.

However, knowledge of the hearing direction R is advantageous not only when adapting and setting a directional hearing operation, as described above, but very generally also when adapting any algorithm A1, A2 that controls the hearing aid 2. This is indicated in FIG. 2 by the further algorithm A2, which is, for example, a noise reduction, a gain, a compression, an audio streaming, a tinnitus algorithm or an own-voice detection.

The following is a summary list of reference numerals and the corresponding structure used in the above description of the invention:

2 Hearing aid
4 Housing
6 Sound tube
8 Microphone
10 Control unit
12 Receiver
14 External appliance
16 Microphone signal
18 Signal
20 Additional sensor
22 Input
24 Output
26 Electrode array
28 Contact
30 Signal pattern
A1, A2 Algorithm
B Mode of operation
H Listening effort
I Intensity of the listening effort
O Ear
R Hearing direction
V Hearing vector

The invention claimed is:

1. A method for operating a hearing aid for a user, which comprises the steps of:
   measuring a neuronal signal of the user and a listening effort of the user is determined therefrom;
   determining both an intensity of the listening effort and a hearing direction from the neuronal signal, wherein the intensity and the hearing direction form a hearing vector; and
   adapting or setting a mode of operation of the hearing aid depending on the hearing direction, for reducing the intensity of the listening effort.

2. The method according to claim 1, which further comprises adapting the mode of operation by virtue of adapting a number of operating parameters of the hearing aid by means of a closed-loop control, wherein the operating parameters are used as manipulated variables and wherein the intensity of the listening effort is used as a controlled variable.

3. The method according to claim 1, wherein the mode of operation is a directional hearing operation, in which sound signals from a direction are output in amplified fashion relative to sound signals from other directions, and the directional hearing operation is adapted by virtue of setting the hearing direction as a direction.

4. The method according to claim 1, wherein the mode of operation is an omnidirectional hearing operation, which is set if a determination of the hearing direction fails.

5. The method according to claim 1, which further comprises assigning the hearing vector on a basis of the hearing direction to one of five directional classes, namely "front", "back", "left", "right" or "unfocused", and in that each of the direction classes has assigned to it the mode of operation, namely "directional hearing to the front", "directional hearing to the back", "directional hearing to the left", "directional hearing to the right" or "omnidirectional hearing", and in that the mode of operation which is assigned to a directional class to which the hearing vector belongs is set.

6. The method according to claim 1, wherein:
   a three-dimensional space around the user is segmented into a plurality of directions, wherein each direction corresponds to a solid angle in the three-dimensional space and wherein each said direction has assigned to it the mode of operation for hearing in a respective direction;
   the hearing vector is represented continuously over the three-dimensional space; and
   the mode of operation which is assigned to the respective direction corresponding to the hearing vector is set.

7. The method according to claim 1, wherein the mode of operation is adapted by virtue of a noise reduction, a gain, a compression, an audio streaming, a tinnitus algorithm or an own-voice recognition being adapted.

8. The method according to claim 1, wherein the mode of operation is adapted or set and in that, in a process or thereafter, a notification is output to the user should the intensity not drop below a lower intensity limit value.

9. The method according to claim 1, wherein the adapting or the setting of the mode of operation is preventable by manual input by the user.

10. The method according to claim 1, wherein the adapting or the setting of the mode of operation is prevented should a certain key situation be present, the key situation being distinguished by a key stimulus that is output to the user irrespective of the listening effort.

11. The method according to claim 1, which further comprises determining the listening effort by means of an electroencephalogram in which the neuronal signal is measured by means of an electrode array, the electrode array having a number of contacts that are disposed at a head of the user and that produce an EEG signal, from which the hearing vector is determined.

12. The method according to claim 11, wherein the EEG signal is a signal pattern and the hearing vector is determined by virtue of the signal pattern measured being compared to a number of signal patterns known in advance.

13. The method according to claim 11, which further comprises disposing the contacts only in a region of at most 5 cm around an ear of the user.

14. The method according to claim 1, which further comprises:
   measuring the neuronal signal on both sides of a head of the user, in each case at an auditory cortex, wherein a right measurement value and a left measurement value are produced; and
   determining the hearing direction by comparing the right measurement value and the left measurement value.

15. The method according to claim 1, which further comprises performing the adapting or the setting of the mode of operation on a basis of an evaluation of a sensor signal of an additional sensor, wherein the sensor signal is classified by virtue of the hearing direction being used as an additional feature.

16. The method according to claim 1, which further comprises carrying out a user-specific optimization, in which the mode of operation is found for the hearing direction, the mode of operation minimizing the intensity of the listening effort for the user, and the mode of operation is stored and set again should a same hearing direction be established again.

17. The method according to claim 1, which further comprises carrying out a situation-specific optimization, wherein the hearing vector is established in a given ambient situation and the mode of operation is determined, the mode of operation minimizing the intensity of the listening effort in the given ambient situation, and the mode of operation is set again in a case of a repeated identification of the given ambient situation.

18. The method according to claim 1, wherein the user belongs to a class of users and the mode of operation is determined in a given ambient situation, the mode of operation minimizing the intensity of the listening effort, and the mode of operation is stored in an external database in order to be set in a case of another user of a same class or in a same ambient situation or in the case of both.

19. The method according to claim 1, wherein the user belongs to a class of users and the hearing aid is set in a given ambient situation by virtue of the mode of operation for precisely the class of users or for precisely the ambient situation or for both being taken from an external database and being used as a starting point for minimizing the intensity.

20. The method according to claim 1, which further comprises determining the listening effort by means of an external evaluation unit.

21. The method according to claim 1, which further comprises determining the listening effort continuously during normal operation of the hearing aid and in that the mode of operation is continuously adapted or set depending on the hearing vector.

22. A hearing aid, comprising:
a control unit programmed to operate the hearing aid for a user, said control unit programmed to:
  measure a neuronal signal of the user and a listening effort of the user is determined therefrom;
  determine both an intensity of the listening effort and a hearing direction from the neuronal signal, wherein the intensity and the hearing direction form a hearing vector; and
  adapt or set a mode of operation of the hearing aid depending on the hearing direction, for reducing the intensity of the listening effort.

* * * * *